(12) United States Patent
Janik (10) Patent No.: US 7,166,838 B1
(45) Date of Patent: Jan. 23, 2007

(54) X-RAY IMAGING FOR PATTERNED FILM MEASUREMENT

(75) Inventor: Gary R. Janik, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 67 days.

(21) Appl. No.: 11/135,974

(22) Filed: May 23, 2005

(51) Int. Cl.
*G01N 23/201* (2006.01)

(52) U.S. Cl. .......................... 250/310; 378/46; 378/90; 378/70; 378/86; 438/14

(58) Field of Classification Search ............... None
See application file for complete search history.

(56) References Cited

U.S. PATENT DOCUMENTS

| | | |
|---|---|---|
| 6,541,286 B1 | 4/2003 | Bernard et al. |
| 6,787,773 B1 | 9/2004 | Lee |
| 6,788,760 B1 | 9/2004 | Janik et al. |
| 2003/0223536 A1 | 12/2003 | Yun et al. |
| 2006/0062351 A1* | 3/2006 | Yokhin et al. ............... 378/86 |

OTHER PUBLICATIONS

Erko et al: "Spatial Structure Of The Bragg-Fresnel Lens" from Diffraction X-Ray Optics, Institute of Physics Publishing, 1996, pp. 73-82.

* cited by examiner

*Primary Examiner*—Jack Berman
*Assistant Examiner*—Zia R. Hashmi
(74) *Attorney, Agent, or Firm*—Bever, Hoffman & Harms, LLP; Jeanette S. Harms (57) ABSTRACT

An x-ray metrology system includes an e-beam generator to cause a test sample to emit x-rays, x-ray optics for focusing the x-rays, and an x-ray imager to generate an image of the test sample from the focused x-rays. Because the x-ray imager provides a direct representation of the x-ray emission characteristics of the test sample, the resolution of a measurement taken using such a sensor is limited only by the resolution of the sensor (and any focusing optics), rather than by the amount of e-beam spread in the thin film. The x-ray imaging can be performed for object planes at the test sample that are not parallel to the test sample, thereby allowing vertical dimension data to be accurately generated by the x-ray imaging system.

20 Claims, 11 Drawing Sheets

X-RAY IMAGING FOR PATTERNED FILM MEASUREMENT

BACKGROUND OF THE INVENTION

1. Field of the Invention

The invention relates to the field of semiconductor metrology, and in particular, to methods and systems for performing metrology on sub-micron semiconductor structures.

2. Related Art

Modern semiconductor metrology techniques must deal with increasingly difficult measurement tasks as the dimensions of integrated circuits (ICs) continue to shrink. Consequently, metrology techniques that might have been acceptable for previous generations of ICs might not be able to handle the latest circuit designs.

For example, copper lines are formed during IC manufacturing as interconnects between devices. Typically, such lines are formed by etching trenches into a dielectric layer, forming an optional barrier layer in the trenches, overfilling those trenches with copper, and then performing chemical mechanical polishing (CMP) to remove the excess copper and create the fine copper lines.

To ensure proper IC functionality, the copper lines formed in this manner must meet strict dimensional requirements for line width and height (i.e., the CMP process must not remove an excessive amount of copper). These dimensional requirements include the requirement that the copper lines not include any voids (i.e., unfilled portions within the trenches) that can increase line resistance. Any barrier layers used in the formation of the copper lines (e.g., to enhance manufacturability, improve electrical performance, and/or reduce copper diffusion) and any subsequent enhancement layers (e.g., cobalt tungsten phosphide (CoWP) formed on top of copper lines to minimize copper diffusion and creep) must meet similar dimensional requirements. However, as the copper lines get increasingly smaller to minimize IC size and enable greater routing complexity, the conventional metrology methods for detecting voids and measuring line profiles (heights) begin to lose their effectiveness.

For example, a conventional method for measuring a patterned film is to direct an electron beam (e-beam) at the film and measure the intensity of the emitted x-rays. By scanning the e-beam over the pattern, the x-ray intensities for different locations in the pattern can be measured. Unfortunately, this method can be less than ideal for modern semiconductor wafers. For example, the e-beam typically spreads out as the beam enters the film. This e-beam "spread" can make the targeting of specific structures or portions of structures in the thin film impossible, thereby preventing conventional tools from being able to resolve the fine details of modern IC device structures. Furthermore, the need to scan the e-beam and take measurements at many locations over the wafer can undesirably increase the metrology time and reduce overall production throughput.

Accordingly, it is desirable to provide a system and method for accurately and efficiently measuring patterned films.

SUMMARY OF THE INVENTION

Conventional x-ray metrology systems can lack the resolution and speed necessary to efficiently and accurately measure the small structures common in modern semiconductor devices. By imaging the x-rays generated in response to a probe e-beam, rather than simply measuring total intensity, the limitations of conventional systems can be overcome. Specifically, because an x-ray imaging sensor (i.e., x-ray imager) provides a direct representation of the x-ray emission characteristics of the thin film, the resolution of a measurement taken using such a sensor is limited only by the resolution of the sensor (and any focusing optics), rather than by the amount of e-beam spread in the thin film.

In one embodiment, an x-ray imaging system can include an e-beam generator for directing an e-beam at a test sample, x-ray optics for focusing the x-rays emitted from the test sample in response to the e-beam, and an x-ray imager for generating an x-ray image of the test sample using the focused x-rays. In various embodiments, the x-ray imaging system can provide various orientations of the test sample relative to the x-ray optics and x-ray imager to allow different object planes at the test sample to be imaged (i.e., allowing different views of the test sample to be generated). In another embodiment, the e-beam generator can selectably provide different e-beam energies and e-beam dimensions to allow for optimized illumination of different types of test sample structures and different test sample regions. In another embodiment, the x-ray imaging system can include additional x-ray optics and x-ray imagers to enable simultaneous or sequential imaging of different views of, or structures in, the test sample. In another embodiment, the x-ray imaging system can include one or more non-imaging x-ray detectors to perform conventional intensity measurements.

A metrology operation on a test sample can be performed by illuminating the test sample with an e-beam and focusing the resulting x-rays onto an x-ray imager to generate an x-ray image. The x-ray image can then be analyzed to determine measurement values for the test sample (e.g., structure thicknesses and/or elemental concentrations) or detect defects that may be present in the test sample. In one embodiment, the imaging can be performed such that the x-ray image represents a top view of the test sample (e.g., to determine thickness or concentration gradients in coatings or layers formed on the test sample). In another embodiment, the imaging can be performed such that the x-ray image represents an angled view of the test sample ("angled x-ray imaging"), thereby allowing height-related characteristics of the test sample to be determined (e.g., void position within a copper line).

A production wafer can include test patterns designed to be used in angled x-ray imaging. The structures in such test patterns can be substantially similar to actual IC structures on the production wafer (i.e., dimensionally similar and created using the same processes), and can be formed in non-functional regions of the production wafer (e.g., scribe lines) to minimize IC area consumption. By spacing the structures in the test patterns to avoid overlapping x-rays during angled x-ray imaging, the analysis required to extract measurement data from the resulting x-ray image can be greatly simplified.

The invention will be more fully understood in view of the following description and drawings.

DETAILED DESCRIPTION

Conventional x-ray metrology systems can lack the resolution and speed necessary to efficiently and accurately measure the small structures common in modern semiconductor devices. By imaging the x-ray generated in response to a probe e-beam, rather than simply measuring total intensity, the limitations of conventional systems can be overcome. Specifically, because an x-ray imager provides a direct representation of the x-ray emission characteristics of the thin film, the resolution of a measurement taken using such a sensor is limited only by the resolution of the sensor (and any focusing optics), rather than by the amount of e-beam spread in the thin film.

Figure 1A:
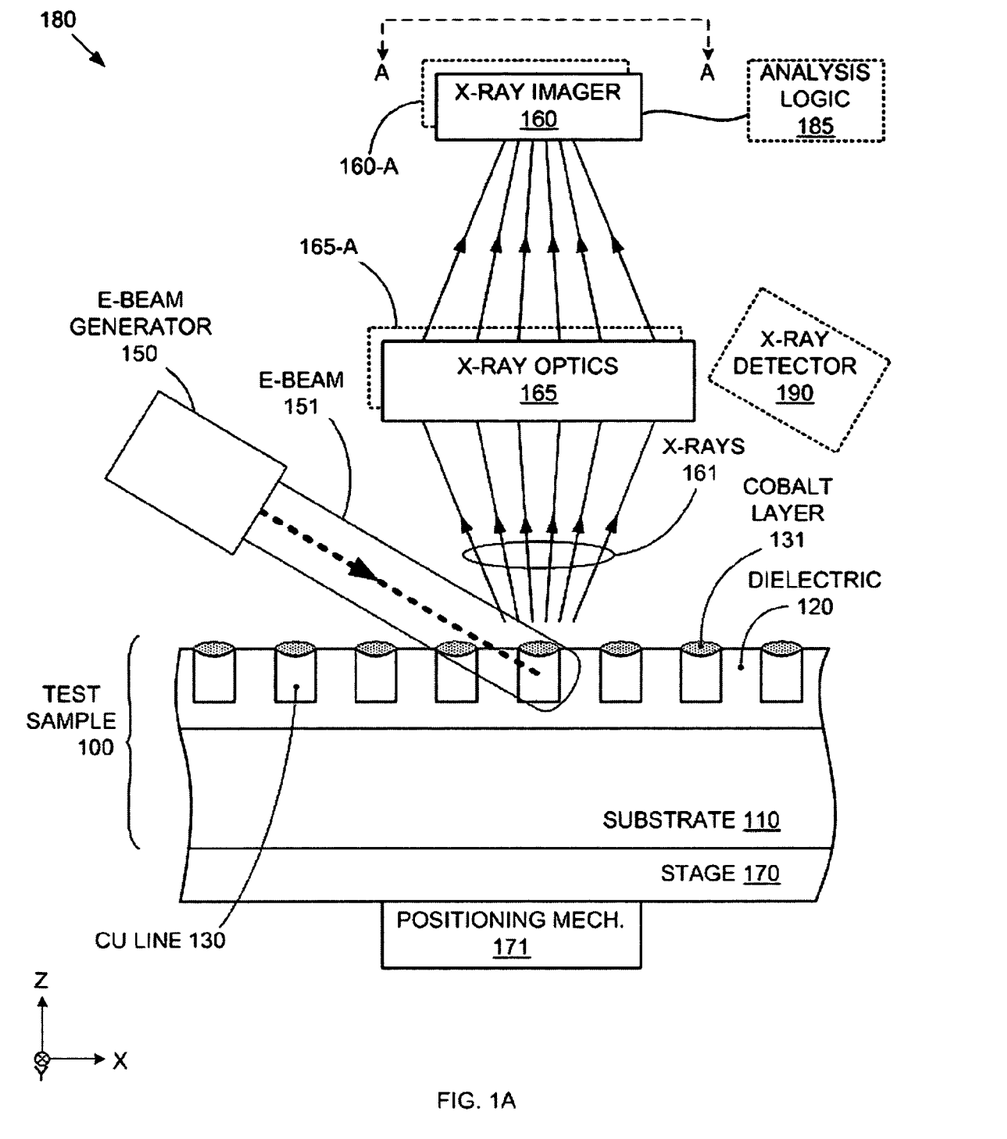
FIG. 1A is a block diagram of a metrology system that includes x-ray imaging capabilities.

FIG. 1A shows an embodiment of an x-ray imaging system 180 that includes an e-beam generator 150, x-ray optics 165, an x-ray imager 160, a stage 170, and optional analysis logic 185. Note that while x-ray imaging system 180 is described below with respect to a single x-ray imager 160 and a single set of x-ray optics 165 for exemplary purposes, according to various other embodiments, x-ray imaging system 180 can include any number of additional x-ray imagers (indicated by dotted line x-ray imager 160-A) and/or any number of additional sets of x-ray optics (indicated by dotted line x-ray optics 165-A). For example, x-ray optics 165-A and x-ray imager 160-A could be used to image a second structure(s) at the measurement location or could be used to image a different view of the same structures being imaged by x-ray optics 165 and x-ray imager 160. Note further that according to various other embodiments, x-ray imaging system 180 can include one or more non-imaging x-ray detectors 190 (indicated by the dotted line) for performing basic x-ray intensity measurements (e.g., to determine elemental composition).

Stage 170 supports and positions a test sample 100 for the measurement operation. Test sample 100 can comprise any type of sample that can generate characteristic x-rays in response to e-beam stimulation. For exemplary purposes, test sample 100 includes a dielectric layer 120 formed on a substrate 110 (e.g., a semiconductor wafer (i.e., a wafer on which semiconductor circuits can be formed, such as a silicon wafer)), and a plurality of copper lines 130 formed in dielectric layer 120. Each of copper lines 130 includes a cobalt layer 131 (such as a cobalt tungsten phosphide (COWP) coating for the prevention of copper diffusion and creep due to electromigration). The thickness and composition of each cobalt layer 131 can vary with copper line pattern density. Therefore, it is desirable to be able to measure the actual cobalt layer thicknesses at different copper lines.

To perform an imaging measurement on test sample 100, e-beam generator 150 directs an e-beam 151 at test sample 100 to cause x-ray emission from test sample 100. Note that in various embodiments, e-beam generator 150 can generate e-beam 151 over a range of selectable energy levels and sizes (e.g., to enable imaging at more than one e-beam energy to determine the depths of imaged features). A set of characteristic x-rays 161 from one or more cobalt layers 131 is then focused by x-ray optics 165 onto x-ray imager 160. X-ray imager 160 can be any type of x-ray sensor that can capture the x-ray pattern provided by x-ray optics 165. For example, in one embodiment, x-ray imager 160 can comprise an array detector that includes an array of detection pixels. Each pixel measures the intensity of the x-rays incident on that pixel, thereby allowing the pixel array to generate a detailed intensity map of the x-ray source (i.e., the portion of test sample 100 illuminated by e-beam 151). The x-ray image can then be analyzed by optional analysis logic 185 (e.g., software running on a computer linked to x-ray imager 160) to determine actual measurement values for test sample 100 or to detect defects in test sample 100.

Note that stage 170 can include a positioning mechanism 171 that can provide any combination of translational, rotational, angular, and height adjustment capabilities to enable optimal positioning of test sample 100 relative to incoming e-beam 151 and also with respect to x-ray imager 160 (and x-ray optics 165). Positioning mechanism 171 can include (or can be controlled by) any type of positioning mechanism(s) and associated position sensor(s). For example, stage 170 could be positioned in the X-Y plane (parallel to test sample 100) by a linear motor positioning system, based on location input from a separate optical microscope used for pattern recognition on the wafer pattern, or from pattern data generated by operating e-beam generator 150 in SEM mode (scanning electron microscope mode). Various other positioning techniques will be readily apparent.

Note further that x-ray optics 165 can include any structures capable of focusing the diverging x-rays 161 onto x-ray imager 160. For example, in one embodiment, x-ray optics 165 can be based on a zone plate objective as described in U.S. patent application Ser. No. 10/157,089, titled "Element-Specific X-Ray Fluorescence Microscope And Method Of Operation" and filed Dec. 4, 2003 by Wenbing Yun et al. In various other embodiments, x-ray optics 165 can be based on x-ray lenses such as those by Adelphi Technologies, Inc., Kirkpatrick-Baez mirror pairs, ellipsoidal mirrors, such as those manufactured by Xenocs SA, toroidal mirrors, Bragg-Fresnel optics, as described in the book "Diffraction x-ray optics" by A. I. Erko et al., or any other type and combination of x-ray focusing elements.

The particular operating parameters for x-ray imaging system 180 will depend on the characteristics of test sample 100. For example, to measure cobalt layers 131, e-beam generator 150 can be configured to generate e-beam 151 with a diameter between 0.5 um and 200 um and an energy between 500 eV and 50 keV. X-ray imager 160 can then be configured to image cobalt La x-rays (x-rays from the La spectral line) having an energy of 0.776 keV. Note that these parameter values are exemplary only, and are not considered to be limiting.

Figure 1B:
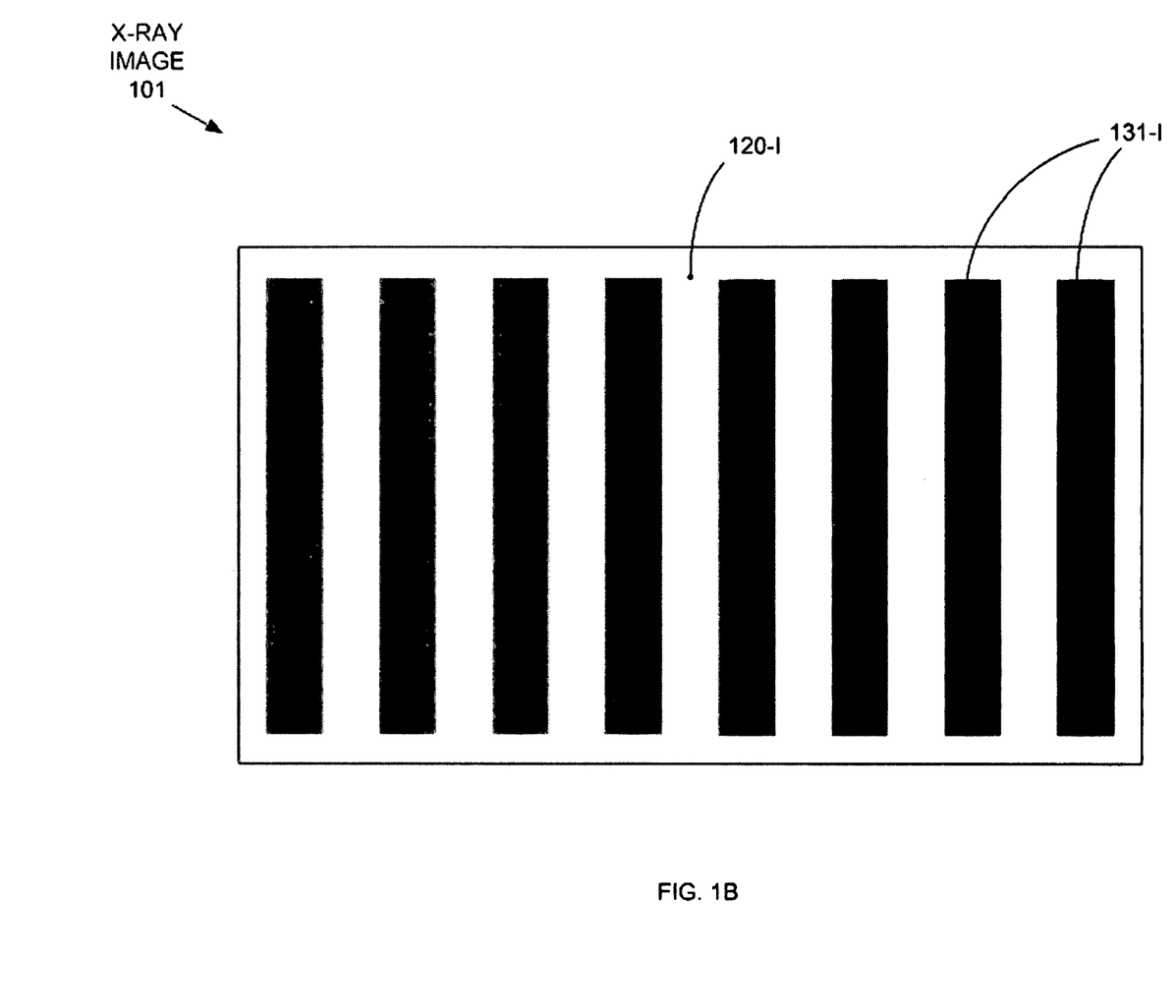
FIG. 1B is a sample x-ray image that could be taken by the metrology system as shown in FIG. 1A.

FIG. 1B shows an exemplary x-ray image 101 (viewed in direction A—A relative to x-ray imager 160 as indicated in FIG. 1A) that could be generated by x-ray imager 160 in response to x-rays 161 emitted by cobalt layers 131 in test sample 100. Darker regions represent regions of greater x-ray intensity, which in turn correspond to areas of greater cobalt thickness in test sample 100. Thus, the region 120-I, which corresponds to dielectric layer 120, is blank, since no cobalt x-rays are emitted from dielectric layer 120. Meanwhile, each shaded region 131-I corresponds to one of cobalt layers 131. Each shaded region 131-I is darker in the middle than at the edges, thereby indicating that each cobalt layer 131 in test sample 100 decreases in thickness from the middle of the layer to the edges of the layer (as shown in FIG. 1A). Note that the shading gradients of regions 131-I in x-ray image 101 can be analyzed by analysis logic 185 more closely to determine the actual thickness variations exhibited by each cobalt layer 131.

For example, analysis logic 185 can include or can access a mathematical model of test sample 100 constructed from discrete regions having expected thickness (or concentration) values. The expected x-ray flux generated by those regions in response to e-beam 151 can then be calculated according to the model, taking into account any absorption of the x-rays by intermediate portions of test sample 100. Analysis logic 185 can then compare the data from measured image 101 to the expected flux, and can vary the thicknesses (or concentrations) in the mathematical model until the model results match image 101. The parameters yielding the best fit can then be provided as the measured values for the thicknesses of cobalt layers 131.

Figure 4:
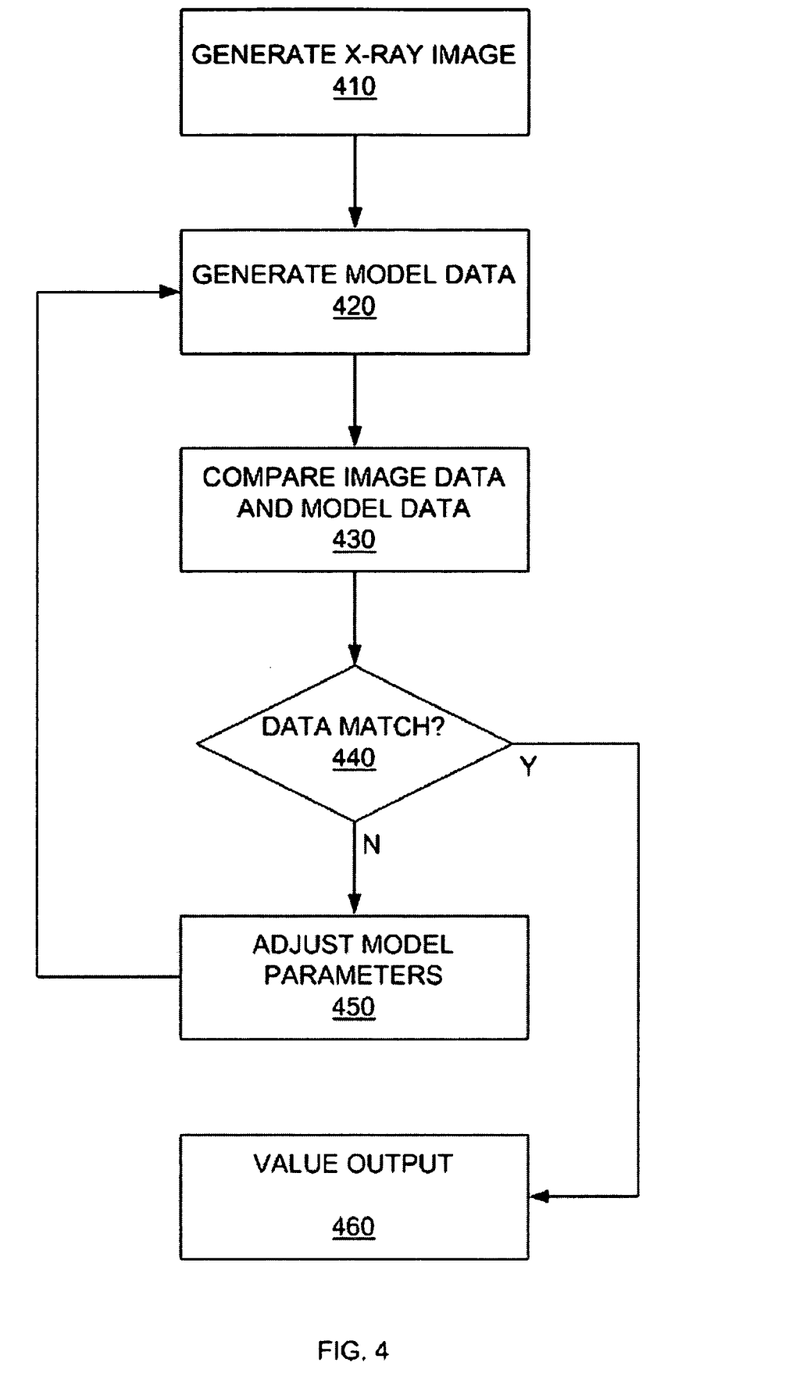
FIG. 4 is a flow diagram of an exemplary method for analyzing x-ray image data for the determination of measurement values.

A flow diagram of this analysis process is depicted in FIG. 4. In a "GENERATE X-RAY IMAGE" step 410, x-ray imaging system 180 generates x-ray image 101, as described with respect to FIGS. 1A and 1B. Meanwhile, analysis logic 185 uses a mathematical model of test sample 100 to generate expected image data in a "GENERATE MODEL DATA" step 420. This model data is then compared to the measured image data (i.e., x-ray image 101) in a "COMPARE IMAGE DATA AND MODEL DATA" step 430. If the model and measured data do not match, a "DATA MATCH?" step 440 causes the mathematical model parameters (e.g., structure dimensions and elemental concentrations) to be varied in an "ADJUST MODEL PARAMETERS" step 450, and the process loops back to step 420. The process continues to iterate in this manner until a match between the model data and the image data is detected in step 440, at which point the model parameters used to generate that model data can be provided by analysis logic 185 as measurement values for the test sample in a "VALUE OUTPUT" step 460.

Returning to FIG. 1A, note that the depicted illumination provided by e-beam 151 (i.e., illuminating two cobalt layers 131) is for exemplary purposes only. For example, in various other embodiments, e-beam generator 150 can be configured to generate an e-beam 151 that illuminates a larger number of cobalt layers 131 (e.g., by defocusing e-beam 151 or simply providing a larger diameter e-beam 151). Increasing the e-beam illumination can allow a larger region of test sample 100 to be imaged (limited by the sizes of x-ray optics 165 and/or x-ray imager 160), thereby increasing measurement throughput.

In this manner, x-ray imaging system 180 can provide a fast, high-resolution evaluation of test sample 100. Because the resolution of the x-ray image 101 generated by x-ray imager 160 is determined by the resolution of x-ray imager 160 (and by the resolution of x-ray optics 165), the capabilities of x-ray imaging system 180 are not restricted by the degree to which e-beam 151 can be focused, or by the spreading of e-beam 151 within test sample 100. Furthermore, increasing the size/coverage of e-beam 151 can actually increase measurement throughput by increasing the portion of test sample 100 being imaged.

Figure 1C:
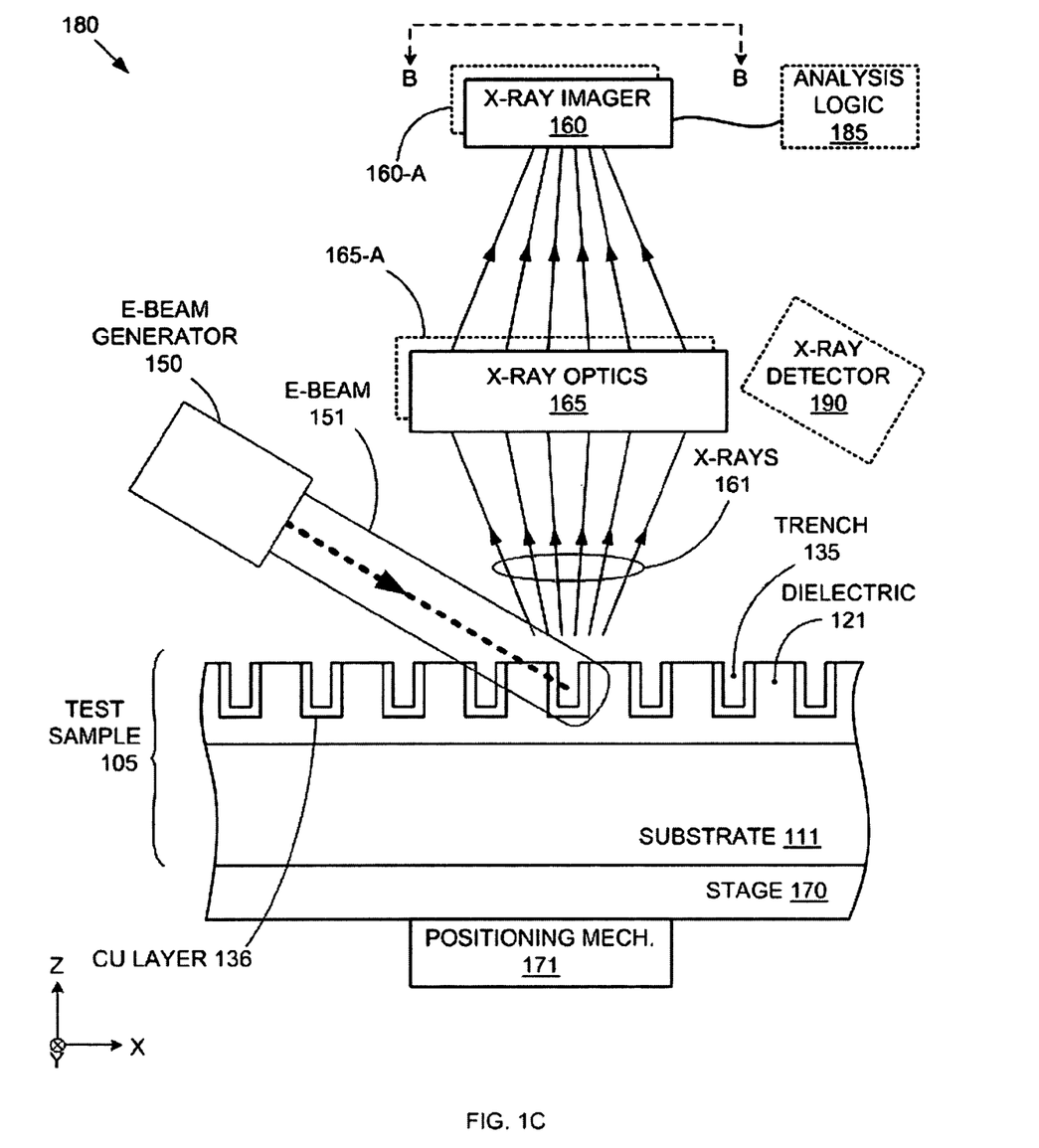
FIG. 1C is the metrology system of FIG. 1A set up to image a different test sample.

FIG. 1C shows x-ray imaging system 180 (as described with respect to FIG. 1A) performing a measurement on a test sample 105. Test sample 105 includes a dielectric layer 121 formed on a substrate 111. Dielectric layer 121 includes multiple trenches 135, with each trench 135 being coated with a copper layer 136. Conventional metrology systems are generally unable to accurately measure the sidewall thicknesses for structures such as copper layers 136. However, the enhanced measurement resolution provided by x-ray imager 160 allows x-ray imaging system 180 to overcome this limitation of conventional systems.

Just as described with respect to FIG. 1A, to perform an imaging operation, e-beam generator 150 directs e-beam 151 at test sample 105. The resulting x-rays 161 are focused by x-ray optics 165 onto x-ray imager 160 to generate an x-ray image that can be used to evaluate the characteristics of copper layers 136.

Figure 1D:
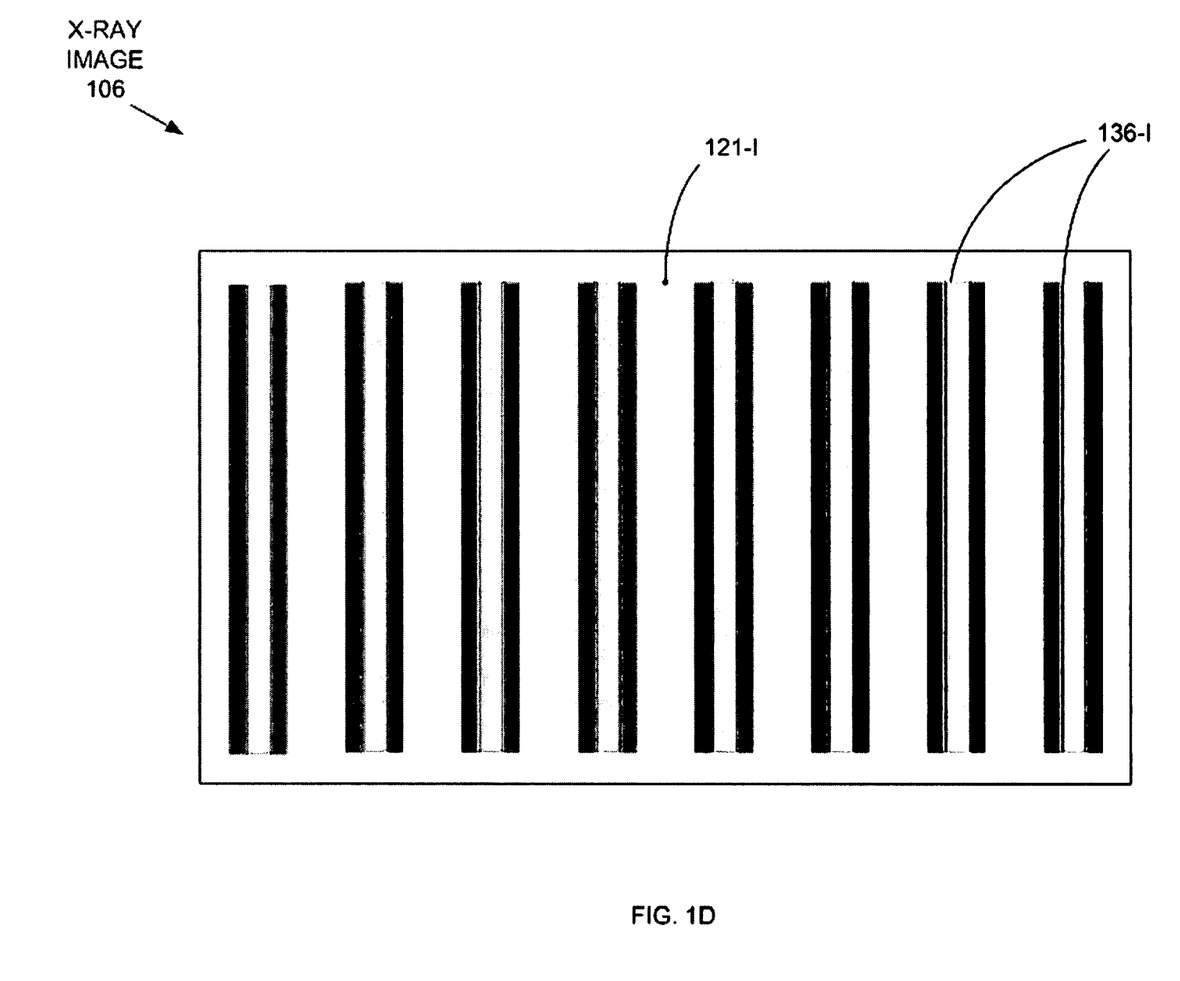
FIG. 1D is a sample x-ray image that could be taken by the metrology system as shown in FIG. 1C.

FIG. 1D shows an exemplary x-ray image 106 (viewed in direction B—B relative to x-ray imager 160 as indicated in FIG. 1C) that could be generated by x-ray imager 160 in response to x-rays 161 emitted by copper layers 136 in test sample 105. Once again, darker regions represent regions of greater x-ray intensity, which in turn correspond to areas of greater copper thickness in test sample 105 (i.e., the sidewalls of copper layers 136). Thus, the region 121-I, which corresponds to dielectric layer 121, is blank, since no copper x-rays are emitted from dielectric layer 121. Meanwhile, each shaded region 136-I corresponds to one of copper layers 136. Each shaded region 136-I is darker at the edges than in the middle, which is indicative of the "U-shaped" configuration of copper layers 136. Therefore, by analyzing shaded regions 136-I (e.g., via mathematical modeling as described above with respect to FIG. 1B), the actual sidewall thicknesses for copper layers 136 can be determined. For example, the widths of the darker regions can be measured to determine the sidewall thicknesses for copper layers 136, while the intensities of the lighter regions can be analyzed to determine the thickness of the bottom layers of copper layers 136. Note that even if the copper layers on the sidewall cannot be fully resolved by the x-ray optical system, the intensities in the darker regions can be used to determine a thickness of the sidewall layers, especially when evaluated in conjunction with a mathematical model of test sample 100.

Figure 2A:
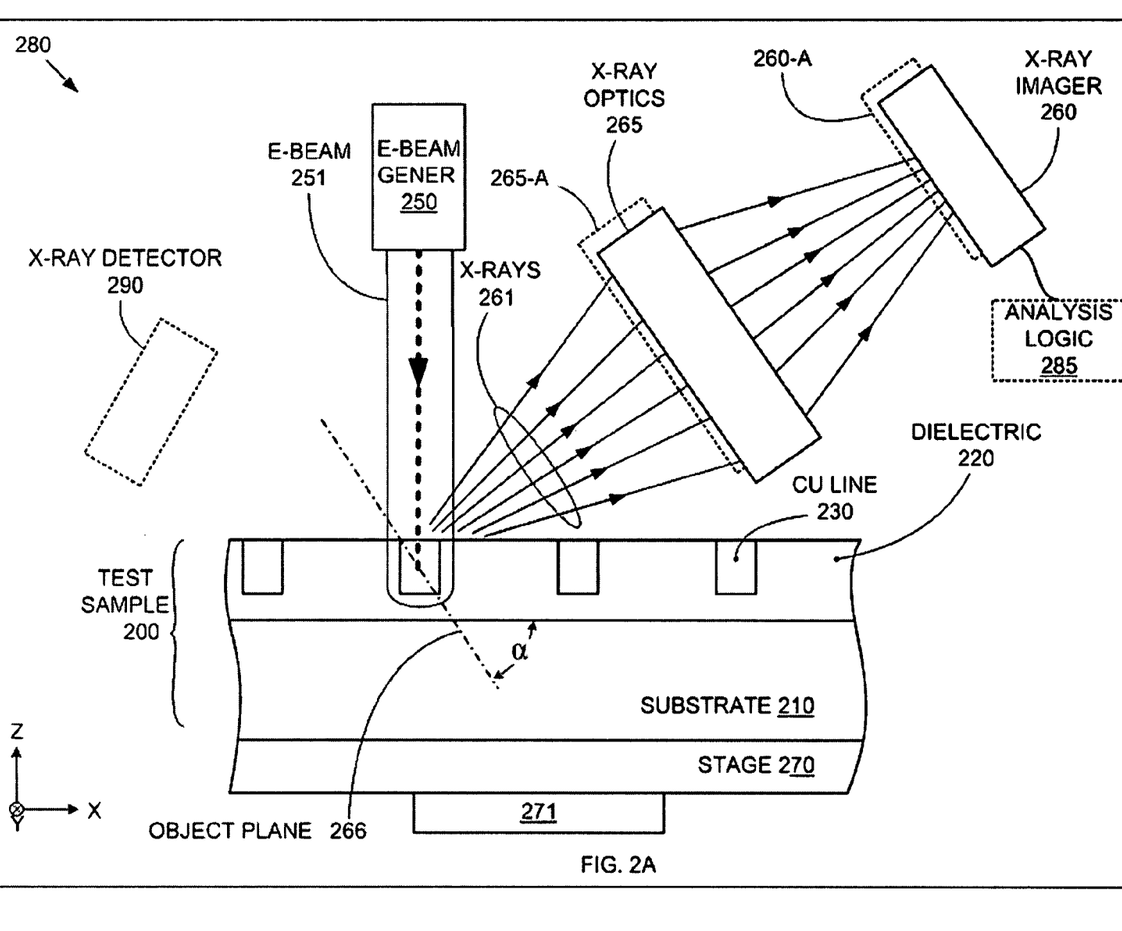
FIGS. 2A, 2B, and 2C are diagrams of a metrology system that includes angled x-ray imaging capabilities.

FIG. 2A shows an embodiment of an x-ray imaging system 280 for measuring a test sample 200. For exemplary purposes, test sample 200 is depicted as including multiple copper lines 230 formed in a dielectric layer 220, which in turn is formed on a substrate 210. X-ray imaging system 280 includes an e-beam generator 250, x-ray optics 265, an x-ray imager 260, a stage 270, and optional analysis logic 285. Note that while x-ray imaging system 280 is described below with respect to a single x-ray imager 260 and a single set of x-ray optics 265 for exemplary purposes, according to various other embodiments, x-ray imaging system 280 can include any number of additional x-ray imagers (indicated by dotted line x-ray imager 260-A) and/or any number of additional sets of x-ray optics (indicated by dotted line x-ray optics 265-A). Note further that according to various other embodiments, x-ray imaging system 280 can include one or more non-imaging x-ray detectors 290 (indicated by the dotted line) for performing basic x-ray intensity measurements (e.g., to determine elemental composition).

To perform a measurement operation, e-beam generator 250 directs an e-beam 251 at test sample 200, which in response emits x-rays 261 that are focused by x-ray optics 265 onto x-ray imager 260. The resulting x-ray image generated by x-ray imager 260 can then be analyzed by analysis logic 285 to determine the physical and/or material characteristics of test sample 200. The material characteristics can be actual measurement values of parameters such as thickness or composition, data regarding the presence or absence of particular defects such as voids or short circuits, or any other information related to the material forming test sample 200. E-beam generator 250, x-ray optics 265, x-ray imager 260, stage 270, and analysis logic 285 are substantially similar to e-beam generator 150, x-ray optics 165, x-ray imager 160, stage 170, and analysis logic 185, respectively, described with respect to FIG. 1A, except that e-beam generator 250, x-ray optics 265, and x-ray imager 260 are positioned relative to stage 270 such that x-ray imager 260 images an object plane 266 of test sample 200 that is not parallel to substrate 210. An "object plane" refers to the plane of an item that can be focused by an imaging system (typically meaning that the object plane is perpendicular to the axis of the focusing optics (e.g., x-ray optics 265)).

For example, the "top view" (X-Y plane) images generated by x-ray imaging system 180 described with respect to FIG. 1A are indicative of an object plane that is parallel to substrate 110 of test sample 100. By defining a non-parallel object plane (i.e., an object plane that is not parallel to the substrate of the test sample (or the test sample itself)), x-ray imaging system 280 can generate x-ray images of test sample 200 that include a "side view" component of the structures within test sample 200. Just as described with respect to stage 170 in FIG. 1A, stage 270 can include a positioning mechanism 271 that can provide any type of positioning mechanism(s) and associated position sensor(s). For example, in one embodiment, stage 270 can include rotational capabilities to allow a variety of views of test sample 200 to be imaged. In one embodiment, the position of x-ray optics 265 and x-ray imager 260 can be adjusted relative to stage 270 to allow any desired object plane angle to be imaged. Note that the angular adjustment range could include imaging capability for an object plane parallel to substrate 210, thereby enabling for x-ray imaging system 280 the top-view x-ray imaging capability described with respect to FIG. 1A.

Figure 2B:
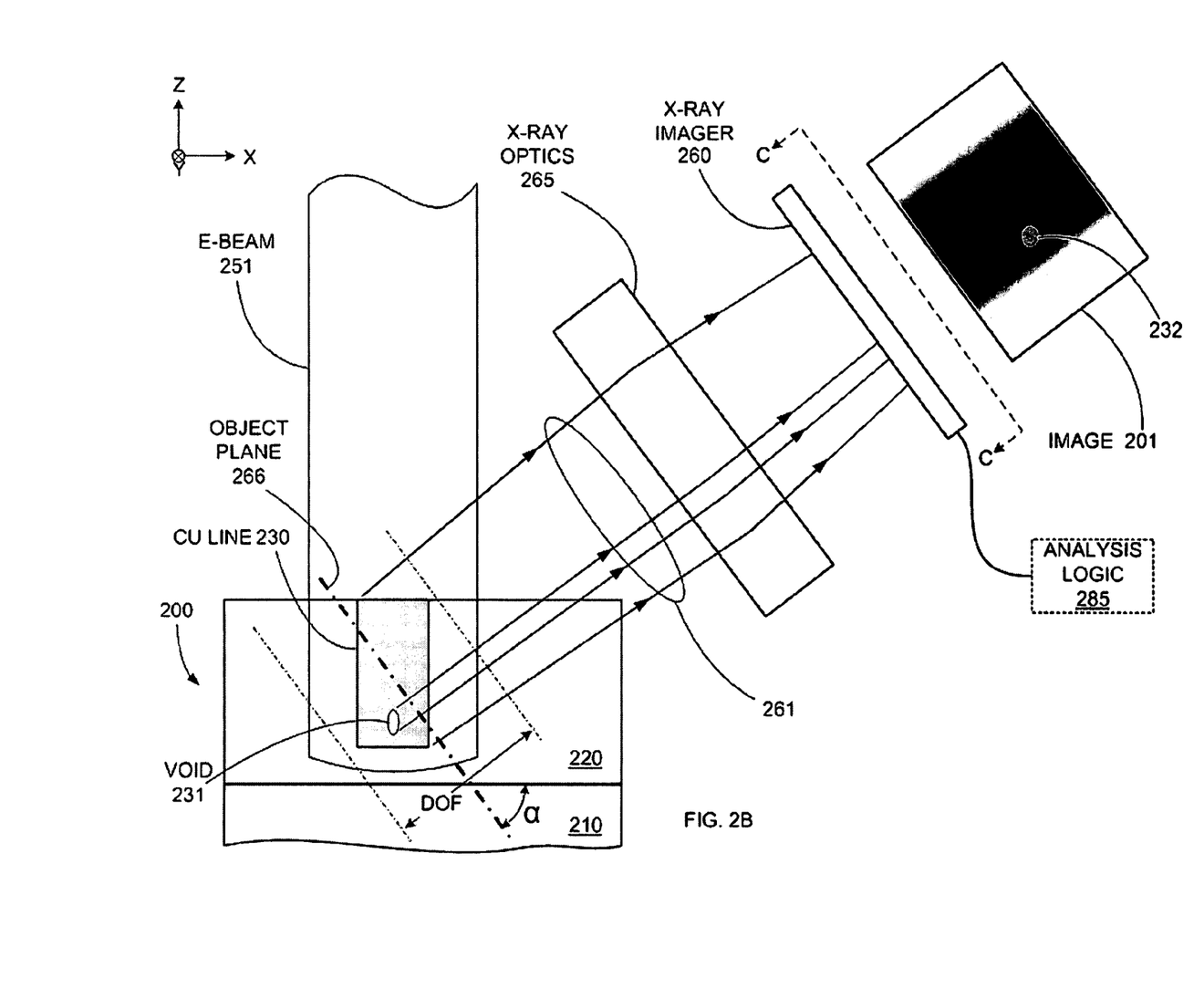

FIG. 2B shows a simplified ray diagram of the imaging operation depicted in FIG. 2A. In FIG. 2B, e-beam 251 illuminates a copper line 230, causing copper line 230 to emit characteristic x-rays 261. X-rays 261 are focused by x-ray optics 265 onto x-ray imager 260. The resulting x-ray image 201 (viewed in direction C—C relative to x-ray imager 260) is presented for reference. X-ray image 201 is generated from an object plane 266 at test sample 200. The depth of field DOF of x-ray optics 265 determines the range of test sample 200 around object plane 266 that can be sharply focused onto x-ray imager 260. In one embodiment, x-ray optics 265 can be selected to have a depth of field larger than the structures being measured (e.g., copper line 230), thereby allowing such structures to be imaged as a whole in a single imaging operation.

Because object plane 266 forms an angle α with substrate 200, image 201 includes information about the characteristics of copper line 230 in the vertical direction (i.e., the Y-Z plane). For example, image 201 includes shaded portions that represent region of test sample 200 from which copper x-ray emissions have been detected. The darker the shading in image 201, the greater the thickness (perpendicular to object plane 266) of copper material in the corresponding region of test sample 200. An abrupt light patch 232 in the midst of darker regions in image 201 can be ray-traced back to a void 231 in copper line 230. Based on the x-ray intensity value(s) associated with patch 232 and the known angle α between object plane 266 and substrate 210, the presence of void 231, and optionally the size of and the Z-axis position of void 231 in copper line 230 can be determined (e.g., by analysis logic 285). A top-view imaging operation (as described with respect to FIG. 1A) would generally not be able to provide such detailed void location information (e.g., distinguishing between a void and a top surface irregularity would be difficult using only a top view image). Thus, by imaging an object plane 266 that is not parallel to test sample 200 (i.e., not parallel to substrate 210), more detailed information can be obtained regarding the interior construction of the structures under observation (e.g., copper line 230).

Figure 2C:
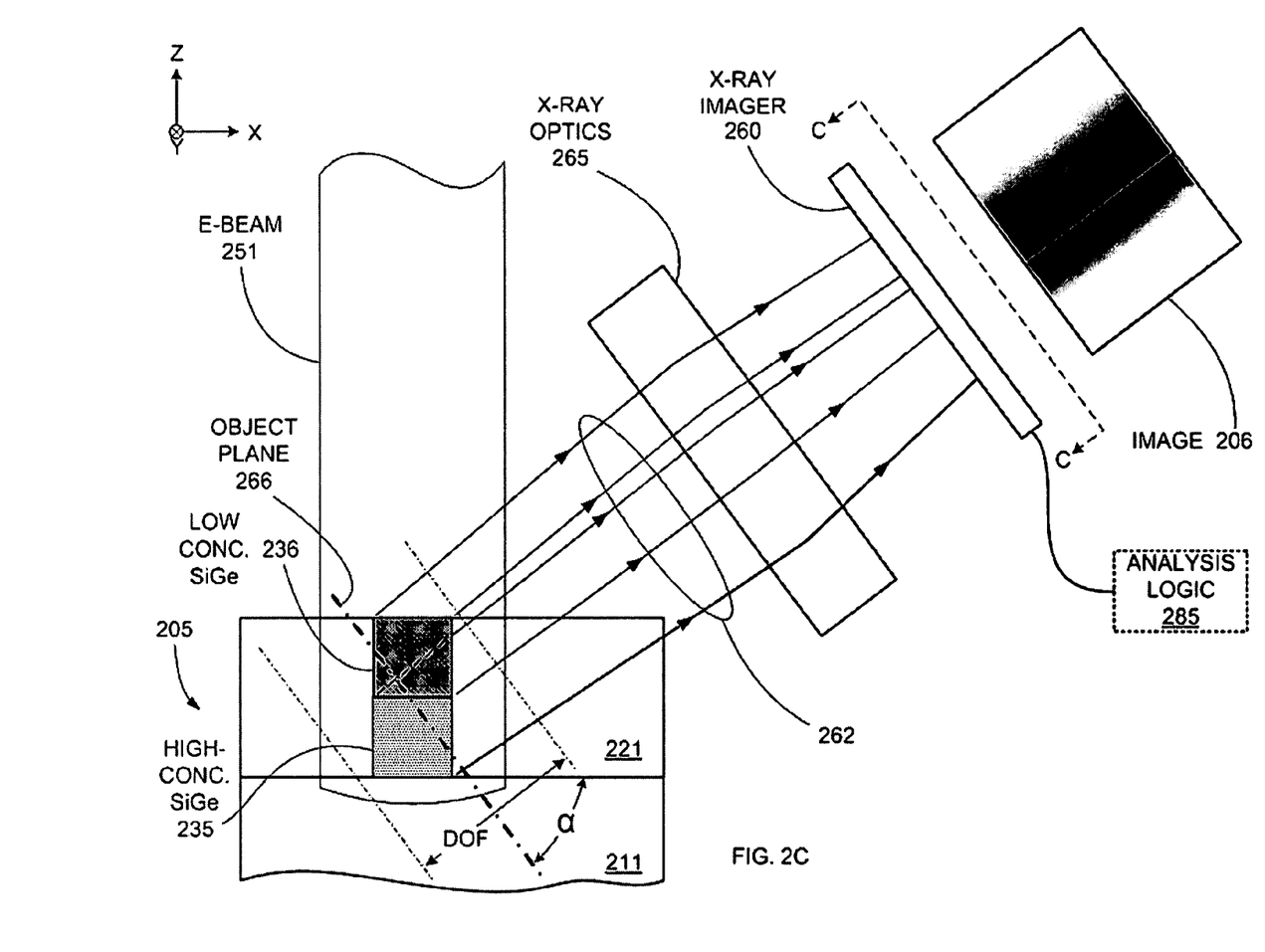

The "angled" imaging capability provided by x-ray imaging system 280 can be beneficially used with any number of different structure types to enable any type of vertical structure data, such as profiling vertical dimensional characteristics or elemental concentration gradients (e.g., boron (B), phosphorous (P), arsenic (As), indium (In), and/or antimony (Sb) dopant concentration distributions). For example, FIG. 2C shows a simplified ray diagram of an imaging operation similar to that depicted in FIGS. 2A and 2B, except that the operation is performed on a different test sample 205. Test sample 205 includes a low germanium concentration silicon germanium (SiGe) layer 236 and a high germanium concentration SiGe layer 235 stacked on a substrate 211 (e.g., a silicon wafer) and surrounded by dielectric or pure silicon material 221. In a manner substantially similar to that described with respect to FIG. 2B, e-beam 251 illuminates the stacked SiGe layers 235 and 236, and the characteristic germanium x-rays 262 (e.g., x-rays at an energy of 1.186 keV) are focused by x-ray optics 265 onto x-ray imager 260. The resulting x-ray image 206 (viewed in direction C—C relative to x-ray imager 260) is presented for reference. The shading (x-ray intensity) gradations of image 206 can then be analyzed to determine the germanium concentration distribution in stacked SiGe layers 235 and 236.

Figure 3A:
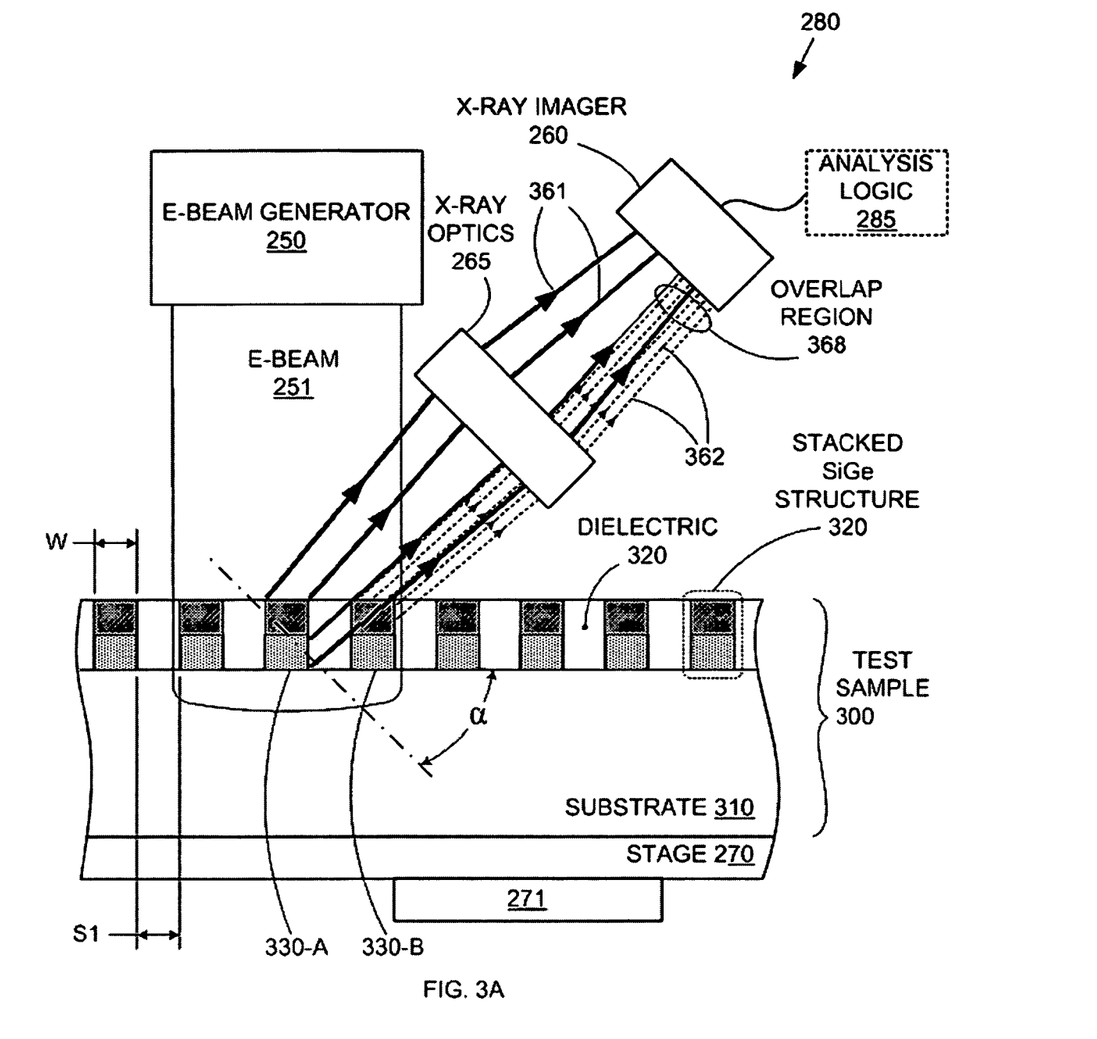
FIG. 3A is a diagram of x-ray shadowing that can occur with angled x-ray measurements.

Note that if a closely-spaced array of structures is present in a test sample, the angled imaging performed by x-ray imaging system 280 may result in x-ray image "shadowing" by adjacent structures. For example, FIG. 3A depicts x-ray imaging system 280 performing a measurement operation on a test sample 300. Test sample 300 includes multiple stacked SiGe structures 320 (e.g., a low germanium concentration SiGe layer formed over a high germanium concentration SiGe layer as shown in FIG. 2C), each having a width W and a spacing S1. During an imaging operation, e-beam 251 generated by e-beam generator 250 may illuminate more than one stacked SiGe structure 320. For example, in FIG. 3A, both structures 330-A and 330-B are illuminated by e-beam 251, and hence, emit a set of x-rays 361 and a set of x-rays 362, respectively. The overlap region 368 between x-rays 361 and x-rays 362 results in an x-ray image of stacked SiGe structure 330-A that is partially shadowed (i.e., overlapped) by an image of stacked SiGe structure 330-B. This shadowing can complicate subsequent analysis of the overall x-ray image by analysis logic 285 (e.g., by requiring more complex and time-consuming modeling). Therefore, in one embodiment, special test structures can be created to eliminate this type of shadowing effect for angled x-ray imaging operations.

Figure 3B:
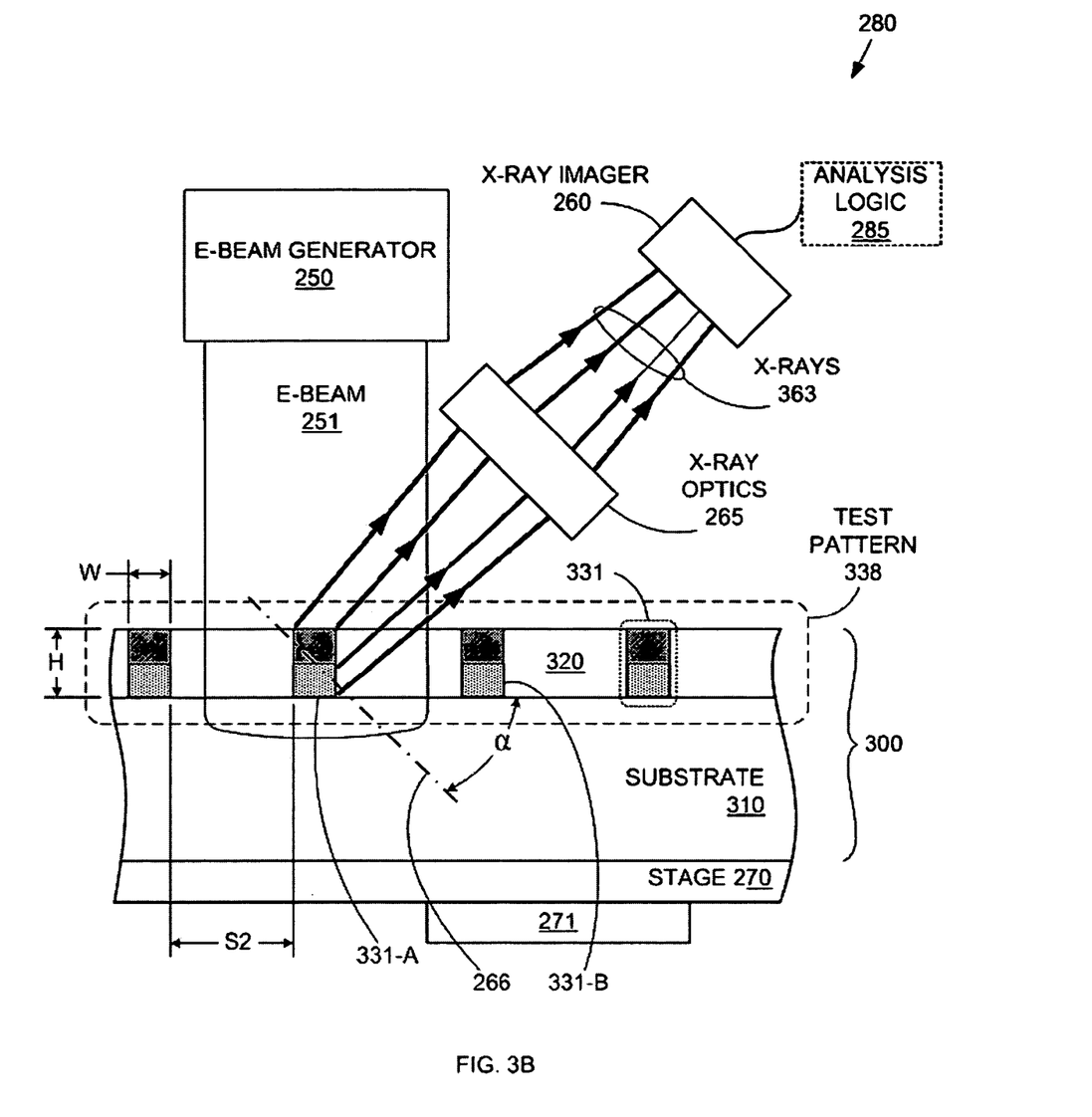
FIGS. 3B and 3C are diagrams of test patterns that can minimize x-ray shadowing in angled x-ray measurements.

For example, FIG. 3B depicts the imaging operation of FIG. 3A being performed on a test pattern 338 in test sample 300. Test pattern 338 includes stacked SiGe structures 331 that are substantially similar to stacked SiGe structures 330 in FIG. 3A (i.e., same size and shape, and formed using the same processes), except that stacked SiGe structures 331 are spaced by a distance S2 that is larger than the spacing S1 of stacked SiGe structures 330. This increased spacing allows x-rays 363 from a stacked SiGe structure 331-A to be imaged by x-ray optics 265 and x-ray imager 260 without any shadowing from adjacent stacked SiGe structure 331-B. In one embodiment, the minimum value S min for the spacing S2 between adjacent structures can be determined by the following equation:

$$S\min = h/\tan(90°-\alpha) \quad \text{[Eqn. 1]}$$

where h is the height of stacked SiGe structures 331 (i.e., the dimension perpendicular to substrate 310), and α is the angle between substrate 310 and the object plane 266 being imaged by x-ray optics 265 and x-ray imager 260. Note that Equation 1 can be applied to any pattern of thin film structures (e.g., copper lines, polysilicon gates, metal gates, dielectric layers, barrier layers, seed layers, vias, plugs, or pads, among others). By selecting a value for spacing S2 that is greater than the minimum spacing value S min, the properties of stacked SiGe structure 331-A can be extracted from the image generated by x-ray imager 260 by analysis logic 285 without having to account for the complications of shadowing by adjacent SiGe structure 331-B.

Figure 3C:
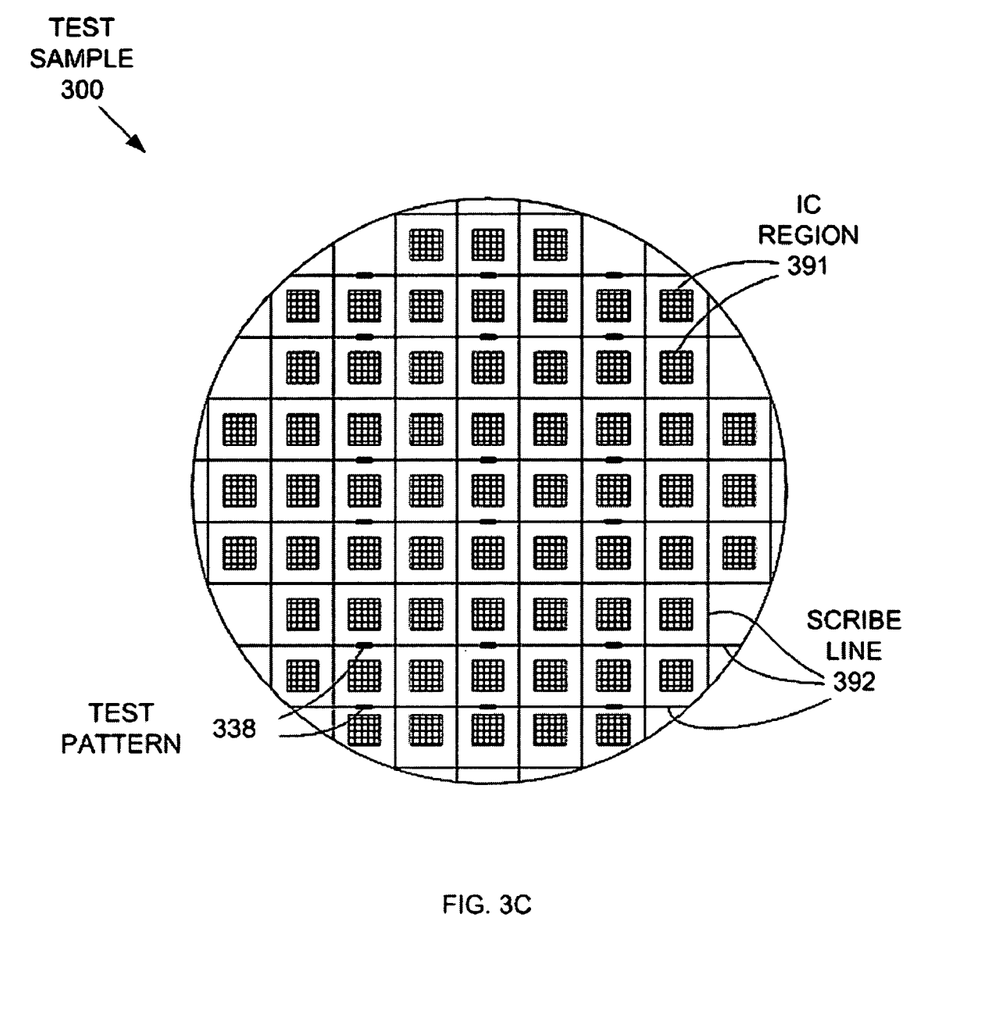

In one embodiment, one or more copies of test pattern 338 can be created in non-functional regions of a production wafer (e.g., test sample 300) for providing process monitoring capabilities without consuming any actual IC area. For example, FIG. 3C shows an exemplary top view of test sample 300 that includes multiple IC regions 391. IC regions 391 are those regions in which functional semiconductor structures are formed. Scribe lines 392 on test sample 300 are also shown. During dicing of test sample 300, IC regions 391 are separated into individual chips by cutting along scribe lines 392. Therefore, scribe lines 392 are non-functional regions of test sample 300, and test patterns 338 can be created in scribe lines 392 as shown. Note that test patterns 338 are depicted as being wider than scribe lines 392 for clarity. In reality, test patterns 338 would typically fit well within scribe lines 392. Note further that the particular arrangement of test patterns 338 is presented for exemplary purposes only. Typically, test patterns 338 would be formed next to each of IC regions 391 (though not all such test patterns 338 would necessarily be analyzed), although any arrangement and any number of test patterns 338 could be created on test sample 300.

Although the present invention has been described in connection with several embodiments, it is understood that this invention is not limited to the embodiments disclosed, but is capable of various modifications that would be apparent to one of ordinary skill in the art. For example, the measurement operations performed using object planes parallel to the substrate described with respect to FIGS. 1A–1D could also be performed using object planes that are not parallel to the substrate (using techniques substantially similar to those described with respect to FIGS. 2A through 3C). Thus, the invention is limited only by the following claims.

The invention claimed is:

1. A system for analyzing a test sample, the system comprising:
   an electron beam (e-beam) generator for directing an e-beam at the test sample to cause the test sample to emit a first set of x-rays;
   a first x-ray imager for generating a first x-ray image from the first set of x-rays; and
   a first set of x-ray optics for focusing the first set of x-rays onto the first x-ray imager.

2. The system of claim 1, wherein the test sample comprises a semiconductor wafer, the system further comprising a stage for supporting the test sample, the stage positioning the test sample such that the first x-ray imager and the first set of x-ray optics are oriented to generate the first x-ray image from an object plane at the test sample that is not parallel to the semiconductor wafer.

3. The system of claim 2, wherein the stage comprises a positioning mechanism for adjusting an angle between the object plane and the semiconductor wafer.

4. The system of claim 2, wherein the stage comprises a positioning mechanism for rotating the test sample.

5. The system of claim 1, wherein the e-beam generator selectably provides at least one of multiple energy levels and multiple beam sizes for the e-beam.

6. The system of claim 1, wherein the first x-ray imager comprises an x-ray array detector.

7. The system of claim 1, wherein the first set of x-ray optics comprise at least one of zone plate optics, x-ray lenses, Kirkpatrick-Baez mirror pairs, an ellipsoidal mirror, a toroidal mirror, or Bragg-Fresnel optics.

8. The system of claim 1, wherein the e-beam is sized to illuminate multiple repeated structures in the test sample, and
   wherein the first x-ray image includes images for at least two of the multiple repeated structures.

9. The system of claim 1, the e-beam further causing the test sample to emit a second set of x-rays, the system further comprising:
   a second x-ray imager for generating a second x-ray image from the second set of x-rays; and
   a second set of x-ray optics for focusing the second set of x-rays onto the second x-ray imager.

10. The system of claim 1, further comprising a non-imaging x-ray detector.

11. A method for performing metrology on a patterned wafer, the method comprising:
    directing an electron beam (e-beam) at a measurement location on the patterned wafer to cause the measurement location to emit a first set of characteristic x-rays;
    focusing a first portion of the first set of characteristic x-rays onto a first x-ray imager to generate a first x-ray image for a first set of structures at the measurement location; and
    analyzing the first x-ray image to generate at least one of a first set of measurement values for the first set of structures and data regarding defect existence in the first set of structures.

12. The method of claim 11, wherein the first set of structures comprises a cobalt layer on a copper line, and
    wherein the first set of measurement values includes a thickness gradient for the cobalt layer.

13. The method of claim 11, wherein the first set of structures comprises a trench formed in a first material, the trench being coated with a layer of a second material, the second material being different from the first material, and
    wherein the first set of measurement values includes a sidewall thickness for the layer of the second material.

14. The method of claim 11, wherein the first x-ray image is of a first object plane at the measurement location that is not parallel to the patterned wafer.

15. The method of claim 14, wherein the measurement location comprises a test pattern, the test pattern comprising a plurality of test structures, the plurality of test structures comprising the first set of structures, adjacent ones of the plurality of test structures being spaced by at least a distance Smin, the distance Smin being given by the equation:

$$S\min = h/\tan(90°-\alpha)$$

where h is a height of the plurality of test structures, and α is an acute angle between the first object plane and the patterned wafer.

16. The method of claim 14, wherein the measurement location further emits a second set of characteristic x-rays in response to the e-beam, the method further comprising:
focusing a portion of the second set of characteristic x-rays onto a second x-ray imager to generate a second x-ray image for a second set of structures at the measurement location; and
analyzing the first x-ray image to generate a first set of measurement values for the first set of structures.

17. The method of claim 14, further comprising focusing a second portion of the first set of characteristic x-rays onto a second x-ray imager to generate a second x-ray image for the first set of structures, wherein the second x-ray image is of a second object plane at the measurement location, the second object plane being different from the first object plane.

18. The method of claim 11, wherein the patterned wafer comprises a plurality of scribe lines, and
wherein the patterned wafer comprises a test pattern formed in one of the plurality of scribe lines, the test pattern comprising the set of structures.

19. The method of claim 11, further comprising measuring a second portion of the first set of x-rays using a non-imaging x-ray detector.

20. A production wafer comprising:
a plurality of functional semiconductor structures formed in a plurality of integrated circuit (IC) locations on the production wafer, the plurality of functional semiconductor structures being formed by a set of process steps; and
a first test pattern for angular x-ray imaging analysis formed in a first non-functional region of the production wafer, the first test pattern comprising a plurality of test semiconductor structures formed by the set of process steps,
wherein each of the plurality of functional semiconductor structures has substantially similar dimensions as each of the plurality of test semiconductor structures, and
wherein adjacent ones of the plurality of test semiconductor structures are spaced by at least a distance Smin, the distance Smin being given by the equation:

$$S\text{min} = h/\tan(90° - \alpha)$$

where h is a height of the plurality of test semiconductor structures, and α is an acute angle between the first object plane for the angular x-ray imaging analysis and the production wafer.

* * * * *